United States Patent
Knight

(10) Patent No.: US 8,162,916 B2
(45) Date of Patent: Apr. 24, 2012

(54) ENTERAL FEEDING SAFETY RESERVOIR AND SYSTEM

(75) Inventor: Thomas F. Knight, Trabuco Canyon, CA (US)

(73) Assignee: Codan US Corporation, Santa Ana, CA (US)

( * ) Notice: Subject to any disclaimer, the term of this patent is extended or adjusted under 35 U.S.C. 154(b) by 728 days.

(21) Appl. No.: 12/028,736

(22) Filed: Feb. 8, 2008

(65) Prior Publication Data

US 2009/0204097 A1     Aug. 13, 2009

(51) Int. Cl.
*A61M 5/32* (2006.01)
(52) U.S. Cl. .................. 604/415; 604/259; 604/910
(58) Field of Classification Search .......... 604/403–415, 604/542, 174, 257, 259, 260–262, 544, 910; 215/11.3, 250, 307, 309, 329; 222/80, 81, 222/478, 189.09
See application file for complete search history.

(56) References Cited

U.S. PATENT DOCUMENTS

| | | | |
|---|---|---|---|
| 3,468,309 A | 9/1969 | Drewe | |
| 3,990,597 A * | 11/1976 | Barton | 215/11.5 |
| 4,335,770 A * | 6/1982 | Kulle et al. | 604/408 |
| 4,558,792 A * | 12/1985 | Cabernoch et al. | 215/11.3 |
| 5,122,123 A * | 6/1992 | Vaillancourt | 604/192 |
| 5,250,037 A | 10/1993 | Bitdinger | |
| 5,782,383 A * | 7/1998 | Robinson | 222/81 |
| 6,238,374 B1 | 5/2001 | Winkler | |
| 6,280,422 B1 * | 8/2001 | Sanchez-Browning | 604/257 |
| RE37,908 E | 11/2002 | Kinsey | |
| 6,599,273 B1 | 7/2003 | Lopez | |
| 6,726,672 B1 | 4/2004 | Hanly et al. | |
| 6,755,804 B2 | 6/2004 | Crawford | |
| 6,773,673 B1 | 8/2004 | Layfield et al. | |
| 6,837,872 B2 | 1/2005 | Crawford | |
| 6,902,207 B2 | 6/2005 | Lickliter | |
| 2004/0054350 A1 * | 3/2004 | Shaughnessy et al. | 604/535 |
| 2004/0123758 A1 | 7/2004 | Shields | |
| 2004/0254525 A1 | 12/2004 | Uber, III et al. | |
| 2007/0282278 A1 | 12/2007 | Knight | |
| 2010/0022984 A1 | 1/2010 | Knight | |
| 2010/0204669 A1 | 8/2010 | Knight | |

OTHER PUBLICATIONS

Color copies of Intopo's website located at the following path: http://eliminatemisconnections.com/intopo.

* cited by examiner

*Primary Examiner* — Tatyana Zalukaeva
*Assistant Examiner* — Benedict L Hanrahan
(74) *Attorney, Agent, or Firm* — Sheppard, Mullin, Richter & Hampton LLP; David E. Heisey

(57) ABSTRACT

The present invention provides a system comprising: a reservoir body configured to hold a reservoir liner, wherein the reservoir liner is configured to hold an enteral feeding material; a reservoir connector configured to connect to the reservoir liner in a manner that permits flow of an enteral feeding material; a reservoir cap configured to connect to the reservoir body in a manner that connects the reservoir connector to the reservoir liner disposed within the reservoir body; and a syringe adapter enteral feeding assembly having a distal end configured to connect to the reservoir cap in a manner that permits flow of the enteral feeding material, and a proximal end configured to connect to an enteral feeding device in a manner that permits flow of the enteral feeding material.

5 Claims, 4 Drawing Sheets

ENTERAL FEEDING SAFETY RESERVOIR AND SYSTEM

FIELD OF THE INVENTION

The invention broadly relates to medical devices, systems and methods and, more particularly, to enteral feeding systems and methods.

BACKGROUND OF THE INVENTION

Enteral feeding is a method of providing nutrition to a person or animal that cannot or will not eat by swallowing. Enteral feeding may be done temporarily, as may be the case for temporary or acute conditions, or indefinitely, as may be the case for chronic or uncurable conditions. An enteral feeding system generally includes a container for holding the feeding material and an apparatus for delivering the feeding material to the patient. One of the major issues with enteral feeding is contamination, as many of the persons or animals that are fed enterally are in a distressed or immunocompromised state. Contamination can result from various sources, but in many cases it results from exposure of the feeding material to an external environment.

SUMMARY OF THE INVENTION

The present invention provides systems and methods for enteral feeding a person or animal. In some embodiments, the systems of the present invention include a reservoir body configured to hold a reservoir liner, wherein the reservoir liner is configured to hold an enteral feeding material; a reservoir connector configured to connect to the reservoir liner in a manner that permits flow of an enteral feeding material; a reservoir cap configured to connect to the reservoir body in a manner that connects the reservoir connector to the reservoir liner disposed within the reservoir body; and a syringe adapter enteral feeding assembly having a distal end configured to connect to the reservoir cap in a manner that permits flow of an enteral feeding material and a proximal end configured to connect to an enteral feeding device in a manner that permits flow of an enteral feeding material. In other embodiments the reservoir liner is pre-filled with an enteral feeding material and sealed. In some such embodiments the reservoir cap is configured to pierce or open the reservoir liner pre-filled with an enteral feeding material. In some embodiments the system also includes an enteral feeding device. In some such embodiments the enteral feeding device is selected from the group consisting of a nasogastric feeding tube, a gastric feeding tube, jejunostomy tube, and a gastrojejunostomy tube. In certain embodiments the syringe adapter enteral feeding assembly is configured to connect only to an enteral feeding device. In some embodiments the syringe adapter enteral feeding assembly is configured to connect only to enteral feeding elements.

In some embodiments, the systems of the present invention include a reservoir body configured to hold a reservoir liner, wherein the reservoir liner is configured to hold an enteral feeding material; a reservoir connector configured to connect to the reservoir liner in a manner that permits flow of an enteral feeding material and prevents substantial exposure to an external environment; a reservoir cap configured to connect to the reservoir body in a manner that permits flow of an enteral feeding material and that connects the reservoir connector to the reservoir liner disposed within the reservoir body in a manner that prevents substantial exposure to the external environment; and a syringe adapter enteral feeding assembly having a distal end configured to connect to the reservoir cap in a manner that permits flow of an enteral feeding material and prevents substantial exposure to the external environment, and a proximal end configured to connect to an enteral feeding device in a manner that permits flow of an enteral feeding material and that prevents substantial exposure to the external environment. In various embodiments the reservoir liner is pre-filled with an enteral feeding material and sealed. In some such embodiments the reservoir cap is configured to pierce or open the reservoir liner pre-filled with an enteral feeding material. In certain embodiments the system also includes an enteral feeding device. In some such embodiments the enteral feeding device is selected from the group consisting of a nasogastric feeding tube, a gastric feeding tube, jejunostomy tube, and a gastrojejunostomy tube. In certain embodiments the syringe adapter enteral feeding assembly is configured to connect only to an enteral feeding device. In some embodiments the syringe adapter enteral feeding assembly is configured to connect only to enteral feeding elements.

In other embodiments the present invention is a method for delivering an enteral feeding material to a patient. In certain embodiments, the method includes the use of a system as described herein. In some embodiments, the present invention is a method for delivering an enteral feeding material to a patient, wherein the enteral feeding medium is not substantially exposed to an external environment. In some such embodiments the methods includes the use of a system as described herein.

In certain embodiments, the methods include the steps of providing a reservoir body having a reservoir liner configured to hold an enteral feeding material; providing a reservoir connector connected with the reservoir liner and a reservoir cap connected to the reservoir connector and the reservoir body; providing a syringe adapter enteral feeding assembly having a proximal end connected to the reservoir liner via the reservoir connector and a distal end connected to an enteral feeding device; engaging the enteral feeding device with a patient in a manner that permits flow of the enteral feeding medium to a patient; and providing the enteral feeding medium to the patient. In some embodiments the methods provide the enteral feeding medium to the patient without substantial exposure to the external environment. In other embodiments the methods provide the enteral feeding medium to the patient without exposure to the external environment.

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

Systems of the present invention have multiple elements and may include a combination of two or more of a reservoir body, a reservoir liner, a reservoir connector, a reservoir cap, syringe adapter enteral feeding assembly, an enteral feeding device and any other compatible device or element. The system of the present invention may include any suitable combination of elements. The elements may be separate so long as they are connectable to form a working system.

Figure 1:
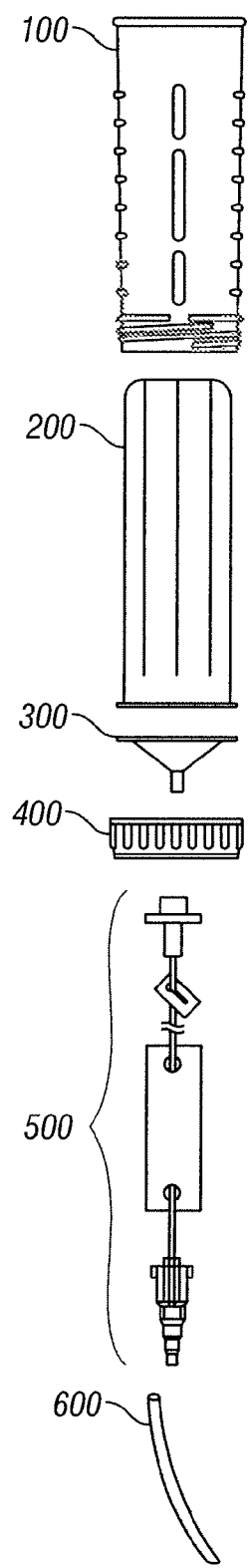
FIG. 1 is a schematic illustration of an embodiment of a system of the present invention.

FIG. 1 illustrates an embodiment of the present invention having reservoir body 100, reservoir liner 200, reservoir connector 300, reservoir cap 400, syringe adapter enteral feeding assembly 500, and enteral feeding device 600. FIG. 1 depicts the various elements of the embodiment of the system. In use, the elements may be connected in any suitable manner. Preferably, each connection will not mate with standard intravenous administration couplings and/or connections. In some embodiments, each connection is unique such that it will only mate and/or connect with elements of an enteral feeding system. In other embodiments, each connection prevents the enteral feeding material from substantial interaction with an environment external to the system and the patient. In various embodiments, each connection prevents the enteral feeding material from any interaction with the external environment. In addition, in some embodiments one or more of the elements is disposable. In other embodiments, each element is disposable.

Figure 2:
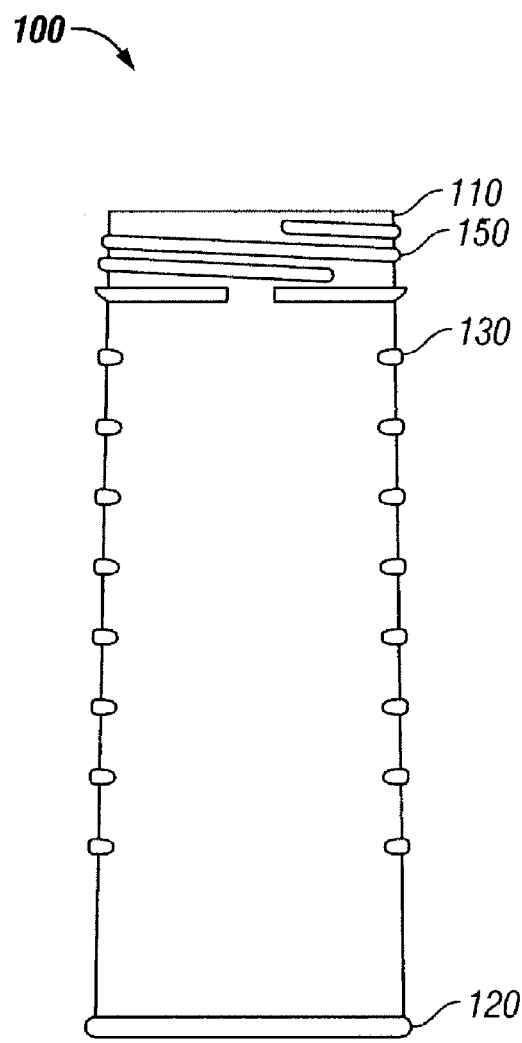
FIG. 2 is an illustration of an embodiment of a reservoir body as may be used in an embodiment of the present invention.

FIG. 2 illustrates an embodiment of reservoir body 100. Reservoir body 100 may be of any suitable size, shape and capacity and may be made of any suitable material. Preferably, reservoir body 100 is made of a rigid material. In some embodiments, reservoir body 100 is made of plastic and has a capacity of about 50 ml to about 2000 ml. Preferably, reservoir body 100 is generally cylindrical in shape, but it may have any suitable shape. Reservoir body 100 is generally hollow such that it defines an area in which reservoir liner 200 may be disposed. Reservoir body 100 has distal end 120 and proximal end 110. References to "proximal" and "distal" elements are made from the perspective of the patient (e.g., reservoir body 100 is distal to enteral feeding device 600). Proximal end 110 may be open or closed. In some embodiments, proximal end 110 includes connection structure 150. Connection structure 150 may be any structure or substance that facilitates connection between reservoir body 100 and reservoir cap 400. In the illustrated embodiment, connection structure 150 comprise threads that interact with corresponding threads 480 on reservoir cap 400 to form a connection. In some embodiments of the invention, distal end 120 is open. In various embodiments, reservoir body 100 has measurement indicators 130 that show the amount of material remaining within reservoir body 100.

Figure 3:
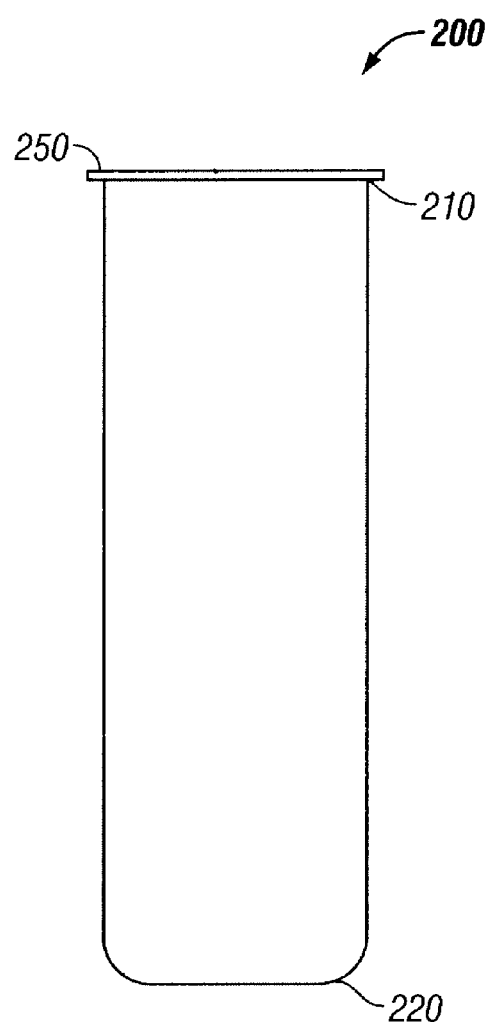
FIG. 3 is an illustration of an embodiment of a reservoir liner as may be used in an embodiment of the present invention.

FIG. 3 illustrates an embodiment of reservoir liner 200. Reservoir liner 200 is configured to hold and dispense enteral feeding material and may be of any suitable size, shape and capacity and may be made of any suitable material. Preferably, reservoir liner 200 is non-rigid and made of plastic. Reservoir liner 200 is configured to fit within reservoir body 100. In preferred embodiments, reservoir liner 200 is substantially cylindrical with a diameter smaller than the diameter of a substantially cylindrical reservoir body 100. Reservoir liner 200 includes distal end 220 and proximal end 210. In preferred embodiments, proximal end 210 has a lip 250 around its circumference. Lip 250 may be made of the same material as the rest of reservoir liner 200 or it may be made of a different material. In preferred embodiments, lip 250 is sized and configured to contact proximal end 110 of reservoir body 100 when reservoir liner 200 is disposed within reservoir body 100. In such embodiments, lip 250 is also configured to contact distal end 320 of reservoir connector 300. In some embodiments, reservoir liner 200 may be physically attached to reservoir body 100. In other embodiments, reservoir liner 200 may be unitary with reservoir body 100. In various embodiments, reservoir liner 200 is pre-filled with enteral feeding material and sealed such that proximal end 320 is closed. In some such embodiments, reservoir liner 200 is sealed using a material that may be pierced or opened as reservoir cap 400 is attached to reservoir body 100.

Figure 4A:
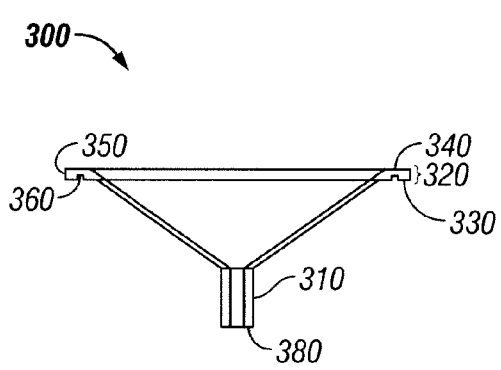
FIG. 4A is a side view of an embodiment of a reservoir connector as may be used in an embodiment of the present invention.
Figure 4B:
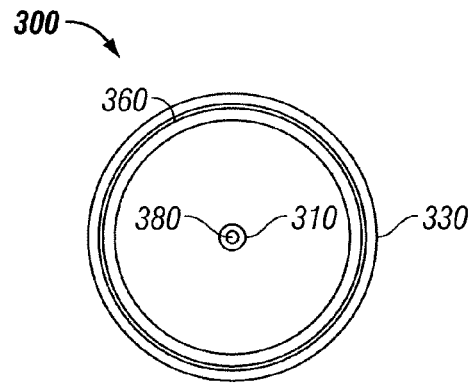
FIG. 4B is a view of the proximal end of an embodiment of a reservoir connector as may be used in an embodiment of the present invention.

FIGS. 4A and 4B illustrate an embodiment of reservoir connector 300. Reservoir connector 300 may be of any suitable size and shape and may be made of any suitable material. In some embodiments, reservoir connector 300 may be attached to or unitary with reservoir cap 400. In such embodiments, the attachment may be made by any suitable method. In the depicted embodiment, reservoir connector 300 has distal end 320 and proximal end 310. Distal end 320 is configured to contract reservoir liner 200 and/or reservoir body 100, whereas proximal end 310 is configured to connect with syringe adapter enteral feeding assembly 500. Preferably, reservoir connector 300 is made of a non-rigid material, such as rubber, and is tapered such that proximal end 310 has a diameter or area that is less than the diameter or area of distal end 320. In the illustrated embodiment, proximal end 310 has aperture 380 and is open at its distal end 320 such that enteral feeding material may enter through distal end 320 and pass through aperture 380. Additionally, distal end 320 includes a lip 350 having a proximal surface 330 and a distal surface 340. In some embodiments, lip 350 is generally circular, is disposed around the circumference or edge of distal end 320 and is sized and configured such that distal surface 340 will contact lip 250 of reservoir liner 200 and proximal surface 330 will contact edge 460 of reservoir cap 460. In some embodiments, proximal surface 330 of lip 350 has annular groove 360 that is configured to mate with annular bump 440 of reservoir cap 400. Reservoir connector 300 may have a structure capable of piercing or opening a reservoir liner 200 that is pre-filled with enteral feeding material and sealed at its proximal end 210.

Figure 5A:
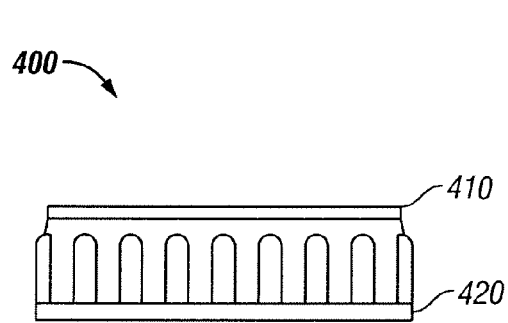
FIG. 5A is a side view of an embodiment of a reservoir cap as may be used in an embodiment of the present invention.
Figure 5B:
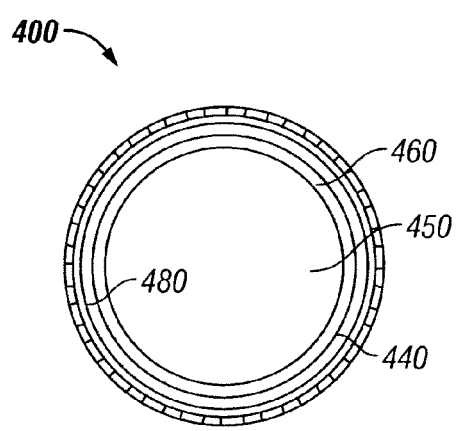
FIG. 5B is a view of the distal end of an embodiment of a reservoir cap as may be used in an embodiment of a system of the present invention.

FIGS. 5A and 5B illustrate an embodiment of reservoir cap 400. Reservoir cap 400 may be any suitable size, shape and configuration and may be made of any suitable material. Reservoir cap 400 is configured to connect with reservoir body 100. In some embodiments, reservoir cap 400 may be attached to or unitary with reservoir connector 300. In preferred embodiments, reservoir cap 400 is rigid and made of plastic. In the depicted embodiment, reservoir cap 400 has proximal end 410 having edge 460 and has distal end 420. In some embodiments, edge 460 is configured to contact the proximal surface 330 of reservoir connector 300 when reservoir cap 400 is connected to reservoir body 100. Preferably, edge 460 has an annular bump 440 which mates with annular groove 360 of reservoir connector 300. Also preferably, the distal end 310 of reservoir connector passes through opening 450 such that distal end 310 is connectable to additional elements, including syringe adapter enteral feeding assembly 500. In preferred embodiments, the connection of reservoir cap 400 to reservoir body 100 is made by interaction of connection structures 150 with threads 480. Preferably, the connection of reservoir cap 400 to reservoir body 100 causes the distal end 320 of reservoir connector 300 to contact lip 250 of reservoir liner 200. Accordingly, in some embodiments, the connection of reservoir cap 400 to reservoir body 100 secures reservoir liner 200 to reservoir body 200, secures reservoir connector 300 to reservoir liner 200 and secures reservoir connector 300 to reservoir cap 400, all in a manner that permits flow of an enteral feeding medium from reservoir liner 200 to the distal end 310 of reservoir connector 300. In preferred embodiments, this connection is such that the enteral feeding medium is not exposed to the external environment. In some embodiments, reservoir cap 400 may have a structure capable of piercing or opening a reservoir liner 200 that is pre-filled with enteral feeding material and sealed at its proximal end 210.

Figure 6:
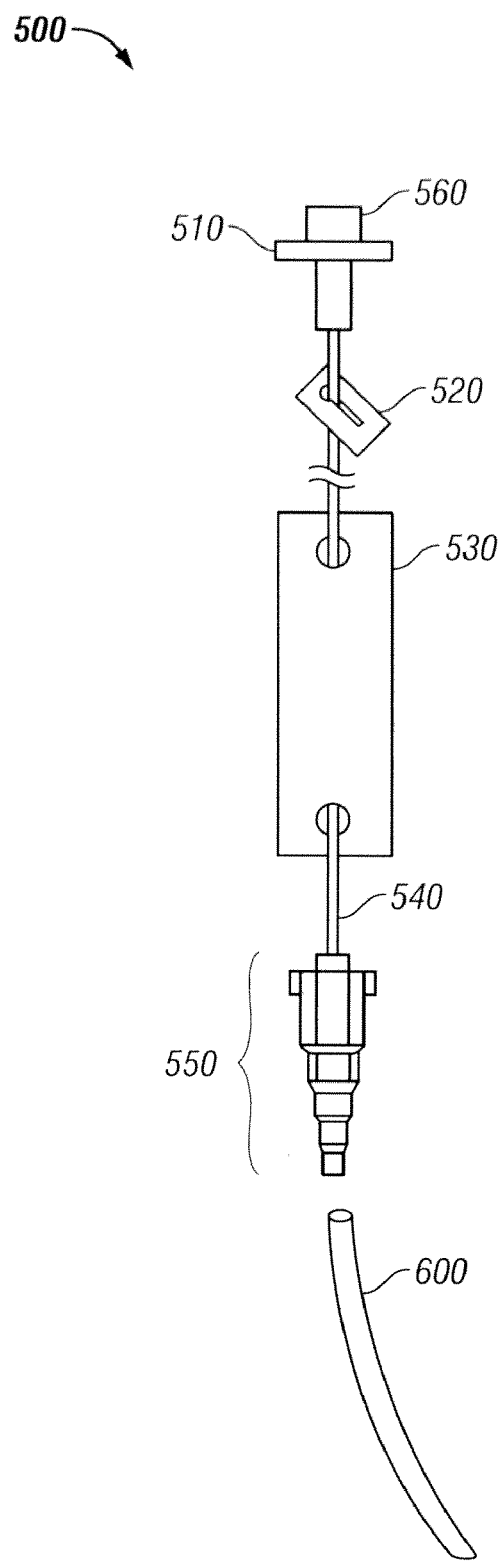
FIG. 6 is a schematic illustration of an embodiment of a syringe adapter enteral feeding assembly as may be used in an embodiment of a system of the present invention.

FIG. 6 illustrates an embodiment of syringe adapter enteral feeding assembly 500. Syringe adapter enteral feeding assembly 500 may be any suitable size and may be made of any suitable material and may have various combinations of elements. The depicted embodiment features syringe adapter 510, clamp 520, warning label 530, tubing 540, and connection member 550. Syringe adapter 510 may be configured as described in U.S. Design Pat. No. D542,406, which is hereby expressly incorporated by reference in its entirety. Preferably, syringe adapter 510 has a distal end 560 configured to connect to reservoir connector 300 and a proximal end configured to connect to tubing 540. Distal end 560 may connect to reservoir connector 300 in any suitable manner. In preferred embodiments, distal end 560 may connect to reservoir connector 300 in a manner that prevents exposure of the enteral feeding medium to the external environment. Clamp 520 may be any suitable clamp. In some embodiments, clamp 520 may be a roller clamp or a slide clamp. Tubing 540 may be made of any suitable material and may have any suitable width, length and thickness. In some embodiments, the tubes may be made of plastic, polyurethane or silicone. In some embodiments, warning label 530 indicates that syringe adapter enteral feeding assembly 500 is to be used for enteral feeding only.

FIG. 6 also depicts an embodiment of enteral feeding device 600. Enteral feeding device 600 may be any suitable device for any suitable method or type of enteral feeding. Enteral feeding device 600 may also include a guide wire assembly to facilitate guiding the assembly into a patient. In some embodiments, enteral feeding device 600 is a nasogastric feeding tube passed through the nares, down the esophagus and into the stomach. In other embodiments, enteral feeding device 600 is a gastric feeding tube inserted through a small incision in the abdomen into the stomach and is used for long-term enteral nutrition. The gastric tube may be any type of gastric tube, including a percutaneous endoscopic gastrostomy tube or a gastronomy tube inserted in an open procedure. In yet other embodiments, enteral feeding device 600 is a jejunostomy tube that is generally surgically inserted into the jejunum rather than the stomach. Enteral feeding device 600 may comprise a dual lumen gastrojejunostomy tube. In some dual lumen embodiments one lumen is a gastric tube and the second lumen is a jujnal lumen. In such embodiments, the gastric lumen is used for decompression and the jejunal lumen is used to administer feedings.

In some embodiments, the present invention is a method of providing a patient with an enteral feeding medium. The enteral feeding medium may be any material suitable for enteral feeding a patient. Such methods may include the use of a system as described herein in enteral feeding a patient. In some embodiments, the methods provide the enteral feeding medium to a patient without substantial exposure of the enteral feeding material to an external environment. Additionally, the methods may provide the enteral feeding medium to a patient without exposure to an external environment.

Thus, it is seen that enteral feeding systems and methods are provided. One skilled in the art will appreciate that the present invention can be practiced by other than the various embodiments and preferred embodiments, which are presented in this description for purposes of illustration and not of limitation, and the present invention is limited only by the claims that follow. It is noted that equivalents for the particular embodiments discussed in this description may practice the invention as well.

While various embodiments of the present invention have been described above, it should be understood that they have been presented by way of example only, and not of limitation. Likewise, the various diagrams may depict an example configuration for the invention, which is done to aid in understanding the features and functionality that may be included in the invention. The invention is not restricted to the illustrated example configurations, but the desired features may be implemented using a variety of alternative configurations. Indeed, it will be apparent to one of skill in the art how alternative functional, logical or physical configurations may be implemented to implement the desired features of the present invention. Also, a multitude of different constituent part names other than those depicted herein may be applied to the various parts. Additionally, with regard to method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead may be applied, alone or in various combinations, to one or more of the other embodiments of the invention, whether or not such embodiments are described and whether or not such features are presented as being a part of a described embodiment. Thus the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives may be implemented without confinement to the illustrated examples. For example, the figures and their accompanying description should not be construed as mandating a particular configuration.

The invention claimed is:

1. A system comprising:
    a reservoir body that holds a reservoir liner, wherein the reservoir liner is pre-filled with an enteral feeding material;
    a reservoir connector connected to the reservoir liner in a manner that permits flow of an enteral feeding material, wherein the reservoir connector is made of a non-rigid material and is tapered downward to an aperture such that a proximal end of the reservoir connector has a diameter less than a distal end of the reservoir connector;
    a reservoir cap connected to the reservoir body in a manner that connects the reservoir connector to the reservoir liner disposed within the reservoir body, wherein the reservoir connector is disposed and held within the reservoir cup; and
    a syringe adapter enteral feeding assembly comprising syringe adapter, tubing and a clamp, the syringe adapter enteral feeding assembly having a distal end connected to the reservoir cap in a manner that permits flow of the enteral feeding material through the tubing, reservoir connector and reservoir cup, and a proximal end connected to an enteral feeding device in a manner that permits flow of the enteral feeding material.

2. The system of claim 1 wherein the reservoir liner is sealed after being pre-filled with the enteral feeding material.

3. The system of claim 1 wherein the proximal end of the syringe adapter enteral feeding assembly is configured to connect only to the enteral feeding device.

4. The system of claim 1 wherein the syringe adapter enteral feeding assembly is configured to connect only to enteral feeding elements.

5. The system of claim 1 wherein the enteral feeding device is selected from the group consisting of a nasogastric feeding tube, a gastric feeding tube, jejunostomy tube, and a gastrojejunostomy tube.

* * * * *